United States Patent [19]

Egan et al.

[11] 4,134,685

[45] Jan. 16, 1979

[54] FLAMELESS ATOMIZATION

[75] Inventors: Edward G. Egan, Mulgrave; Ian S. Jackson, Glen Waverley; Peter Bennett, Glen Iris, all of Australia

[73] Assignee: Varian Techtron Proprietary Limited, Springvale, Australia

[21] Appl. No.: 751,761

[22] Filed: Dec. 16, 1976

[51] Int. Cl.² ............................................... G01J 3/30
[52] U.S. Cl. .................................................... 356/312
[58] Field of Search .......................................... 356/85

[56] References Cited
PUBLICATIONS

Culver et al., *American Laboratory*, vol. 8, No. 3, Mar. 1976, pp. 59-62, 64 and 66-69.

*Primary Examiner*—F. L. Evans
*Attorney, Agent, or Firm*—Stanley Z. Cole; Gerald M. Fisher; John J. Morrissey

[57] ABSTRACT

Chemical analysis apparatus such as a spectrophotometer, having a carbon rod or other non-flame atomizer which is adapted to be heated by electrical resistance heating. The atomizer is included in a heater circuit, and a particular relationship exists between the electrical resistance of the atomizer and the electrical resistance of the remainder of that circuit. That relationship is such that variations in the atomizer resistance as may occur over a period of use, do not substantially affect power dissipation in the atomizer during heating. Ideally, the two resistance values are equal, but variations from the ideal are satisfactory in practice. A feed-back circuit is arranged to maintain a substantially constant voltage across the heater circuit, and that is achieved by comparing the applied voltage with a reference voltage and modifying the applied voltage as necessary to maintain a predetermined relationship between the two.

11 Claims, 6 Drawing Figures

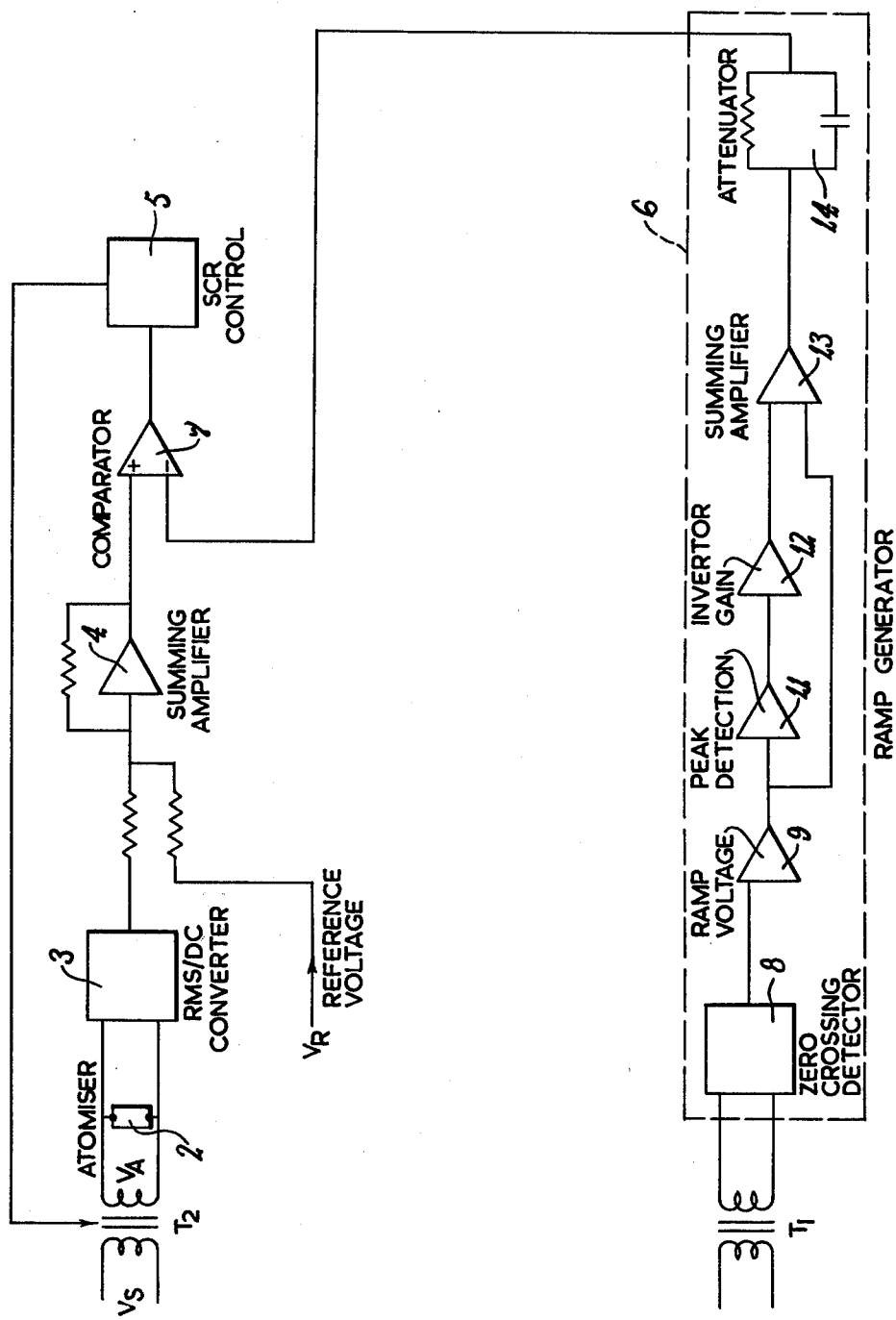

FLAMELESS ATOMIZATION

This invention relates to a method and apparatus for use in flameless atomization of materials, and is especially applicable in chemical analysis equipment such as spectrophotometers, but may have other uses. It will be convenient to hereinafter describe the invention in relation to atomic absorption spectrophotometers.

In atomic absorption spectrophotometers employing flameless atomization, the atomizer is often formed by a carbon element, and the sample to be analyzed is deposited on or within that element usually in the form of a solution. Atomization of the sample in the light path of the instrument results in production of an absorption signal and the peak height or area of the signal is usually taken as a measure of the concentration of the element of interest in the sample solution. Under ideal conditions, the peak height or area of the signal is linearly related to concentration.

Good reproducability of the absorbance signal is determined by the stability and controlability of the temperature of the carbon element atomizer, and the stability of that work head of the instrument upon which the atomizer is mounted. A major problem encountered is variation of the set temperature of the atomizer resulting from fluctuations in mains voltage and other factors influencing the atomizer power supply.

It is therefore a principal object of the present invention to provide means whereby the temperature of flameless atomizers can be accurately controlled. In application to chemical analysis by atomic absorption, that control facility enables more reproducable determination of absorbance.

The present invention relies on the fact that the atomizer temperature is dependent upon the power supplied, and involves the application of a feed-back system whereby that power can be controlled. The invention further relies upon the discovery that the variable resistance components of the total resistance of the circuit can be related to the fixed resistance components, so that the effect of fluctuations in any of the variable resistance components will be minimized. As a result, such fluctuations will cause relatively small changes in the power in the work head, and the consequent temperature of the element being heated.

In accordance with one aspect of the present invention, there is provided chemical analysis apparatus including; an atomizer for receiving a sample to be analyzed; a heater circuit which includes said atomizer and is connectable to an electrical power source so that said atomizer is heated by resistance heating, the total electrical resistance of said circuit being the sum of the atomizer resistance and a further resistance which is the electrical resistance of that part of said circuit other than said atomizer, and said further resistance is preselected relative to said atomizer resistance such that operational variations of said atomizer resistance do not substantially affect power dissipation in said atomizer during heating thereof; and a feed-back system connectable to said power source and being operative to maintain a substantially constant voltage across said heater circuit during heating of said atomizer.

In accordance with another aspect of the invention there is provided, a method of sample analysis including the steps of; connecting an atomizer in series with an electrical resistance having a resistance value of no less than half and no more than twice the initial resistance value of said atomizer; said atomizer and said electrical resistance forming a heater circuit; connecting said heater circuit to an electrical power source to heat said atomizer by electrical resistance heating; maintaining a substantially constant voltage across said heater circuit; and introducing a sample to be analysed to said heated atomizer.

The reference to "operational variations" of the atomizer resistance, is to be understood as meaning the changes which occur in the electrical resistance value of the atomizer as a consequence of its use or operation. That is, the preselected relationship between the two resistances (i.e., fixed and variable resistances) is established before the atomizer is actually put into use, and consequently the reference resistance of the atomizer is its "initial resistance". When carbon rod atomizers are heated by resistance heating, it is found that the electrical resistance of the atomizer varies with time due to erosion, build-up of deposits, and other factors. As a result of that change in resistance, the power dissipation within the atomizer usually changes, with consequent effect on the furnace temperature. When the concept of the present invention is applied to such an arrangement, such "operational" variation in atomizer resistance has minimal effect on the power supplied to the atomizer, and consequently the atomizer or furnace temperature is maintained substantially constant.

The essential features of the invention, and further optional features, are described in detail in the following passages of the specification which refer to the accompanying drawings. The drawings however, are merely illustrative of how the invention might be put into effect, so that the specific form and arrangement of the features (whether they be essential or optional features) shown is not to be understood as limiting on the invention.

In the drawings:

FIG. 2 is a more detailed diagrammatic form of the circuit shown in FIG. 1.

Figure 1:
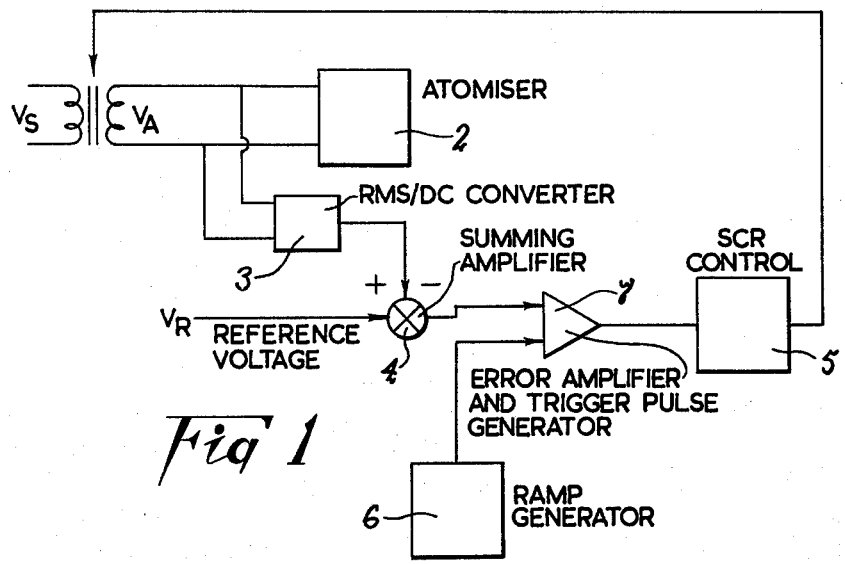
FIG. 1 shows, in diagrammatic form, an example circuit layout incorporating the invention.

As previously stated, the invention broadly involves arranging the total resistance of the atomizer circuit so that variations in the atomizer resistance has minimum effect on power dissipation in the atomizer, and providing a feed-back system whereby the applied voltage is controlled to maintain substantially constant power dissipation in the atomizer. The circuit involves two principal elements of resistance, one of which contributes to the heating of the atomizer and may vary due to a number of factors such as the type of carbon used, contact resistance between the tube and supply electrodes, and the effect of use on the tube resistance due to erosion of the carbon. That variable principal resistance is referred to throughout this specification as the "atomizer resistance", whereas in fact components other than the actual atomizer element (e.g., carbon rod) may contribute to the total value of that resistance. The other principal element comprises or includes a fixed resistance which is preset to provide the necessary compensation for changes in the heating resistance.

Ideally the fixed resistance is equal to the nominal resistance of the atomizer (i.e., the calculated value of the atomizer resistance before use), but that exact relationship is not essential for successful application of the invention. It is to be understood that the fixed resistance is the resistance in the total circuit other than that inherent in the atomizer.

The following mathematical explanation may assist in understanding the basic concept of the invention.

Assuming that the voltage applied across the total resistance circuit is maintained constant, the power causing heating of the furnace will be $I^2R_V$, where:

I is the current through the circuit, and
$R_V$ is the furnace resistance.

The total resistance of the circuit can be expressed as $R_V + R_F$, where $R_F$ is the fixed resistance, so that:

$$I = V/R_V + R_F,$$

where V is the aforementioned applied voltage.

Thus, the heating power can be expressed as $$P = (V/R_V + R_F)^2 \cdot R_V$$

If $R_F$ is assumed to be constant, a condition can be found as follows under which the furnace resistance $R_V$ can vary without substantially affecting the heating power and consequently the furnace temperature.

$$\frac{\partial P}{\partial R_V} = \frac{V_A^2[(R_F + R_V)^2 \cdot 1 - 2R_V(R_F + R_V) \cdot 1]}{(R_F + R_V)^2} = 0$$

$$\therefore R_F + R_V = 2R_V$$

$$\therefore R_F R_V.$$

It can be shown by calculation that, for excursions of $R_V 2R_F$ and $0.5R_F$ (i.e., 4:1 change) the power will drop by approximately 12%. In actual practice however, when the present invention is applied to a spectrophotometer, it is preferred that the maximum excursion range of $R_V$ is 2:1, so that the maximum drop in power is greatly reduced.

An appropriate value of $R_F$ can be determined by trial and error. That is, in an actual circuit, $R_F$ can be increased from a minimum value until a condition is found at which there is minimum variation of furnace temperature with changes in furnace resistance.

Control of the applied voltage may be achieved in any appropriate manner, but in the preferred arrangement shown in FIG. 1 of the accompanying drawings, that is achieved by a feed-back circuit which responds to the voltage $V_A$ applied across the atomizer 2. That feed-back circuit is arranged to respond to the root mean square of the applied voltage $V_A$ (i.e. the RMS voltage) rather than the average voltage, as only the former has a direct relationship to the power dissipation in the atomizer 2, and consequently the temperature of the atomizer 2.

The particular feed-back circuit shown, includes converter means 3 for converting the RMS voltage to D.C. voltage and introducing that D.C. voltage to a summing amplifier 4 which also receives a predetermined reference voltage $V_R$. The reference voltage $V_R$ is selected to be proportional to the applied voltage $V_A$ as calculated to provide the necessary power to the atomizer 2. The output of the summing amplifier 4 is connected to control means such as a silicon controlled rectifier (S.C.R.) control 5 which is operatively connected into the heater circuit to influence the power supplied to the atomizer 2.

In the circuit of FIG. 1, any drop in the RMS applied voltage will result in an increased error signal emanating from the summing amplifier 4, and because of that signal, the trigger pulse is advanced which causes the S.C.R. 5 to fire earlier and thereby increases the RMS voltage applied to the heater circuit, consequently causing an increase in power applied to the atomizer 2. The same type of effect will result if the RMS applied voltage exceeds the reference voltage $V_R$, but of course the influence on the heating circuit will be of the reverse order.

In general, the feed-back circuit, regardless of its specific form, is intended to sense fluctuations in the RMS voltage, and to apply a corrective influence to the heater circuit to compensate for such fluctuations.

FIG. 2 shows a particular form of the general circuit shown in FIG. 1, and especially shows greater detail in respect of the ramp generator 6 which is part of the feed-back system in FIG. 1. The ramp generator 6 and the summing amplifier 4, are both connected to a comparator 7 (also shown in FIG. 1) which has its output connected to the S.C.R. control 5. The primary function of the ramp generator 6 is to ensure that the S.C.R. control 5 fires to modify the applied voltage $V_A$ at the appropriate time in the AC cycle of the power supply generating $V_A$. For example, the power supply may be a conventional mains supply, in which event the transformer $T_1$ which drives the ramp generator 6, is connected into that supply.

Figure 3:
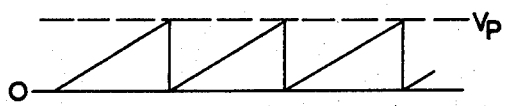
FIG. 3 is a diagrammatic representation of the signal wave form at the output of the ramp voltage amplifier of the FIG. 2 circuit.
Figure 4:
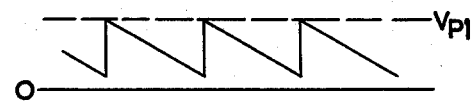
FIG. 4 is a diagrammatic representation of the signal wave form at the output of the summing amplifier of the FIG. 2 circuit.

Synchronization of the ramp generator 6 with the mains current is achieved, in the circuit shown, through a zero crossing detector 8 which operates to generate a signal each time the supply voltage reaches zero. Thus, a series of regularly spaced signals results, and those signals are received by a ramp voltage amplifier 9 which functions to produce a signal of saw-tooth form as shown in FIG. 3. That is, the output of the amplifier 9 comprises a series of ramp voltage signals which short to zero from a peak voltage $V_p$. The amplifier 9 output is passed through peak detector and gain invertor amplifiers 11 and 12 respectively, to a summing amplifier 13, all of which function in a known manner to produce a signal of wave form as shown in FIG. 4. The primary purpose of the gain invertor amplifier 12 is to ensure that the resulting voltage signal does not fall below zero — for example the base of the signal may be held at +0.4 volts.

The output of the summing amplifier 13 is received by an attenuator 14 which modifies the signal wave form by creating a "pip" 15. As a result of that modification, full drive conduction is achieved as hereinafter explained.

Figure 6:
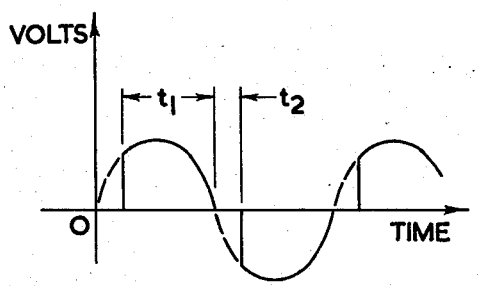
FIG. 6 is a diagrammatic representation of the signal wave form on the power source input of the atomizer, as modified by the feed-back system of the FIG. 2 circuit.

The signals from the ramp generator 6 and summing amplifier 4 are received by the comparator 7 and a pulsed signal results which is used to trigger S.C.R. control 5. The signal from the ramp generator 6 ensures that the output of the comparator 7 fires or triggers the S.C.R. control 5 at a suitable time in each cycle of the power supply current. FIG. 6 shows, by way of example, how the voltage applied to the atomizer 2 is controlled by the S.C.R. control 5. The S.C.R. control 5 fires over each time period $t_1$, and application of the supply voltage to the atomizer 2 is delayed over each time period $t_2$, and the S.C.R. control 5 varies those time periods as necessary to ensure a substantially constant voltage across the atomizer 2.

Figure 5:
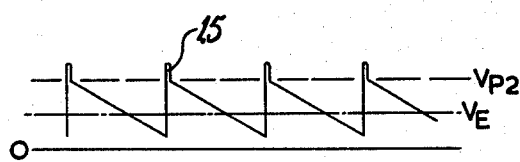
FIG. 5 is a diagrammatic representation of the signal wave form at the output of the attentuator of the FIG. 2 circuit.

In FIG. 5, $V_E$ represents an amplified voltage which is characteristic of the difference between $V_R$ and $V_A$, and is in effect the output of the summing amplifier 4. Assuming the circuit shown in the drawings forms part of a spectrophotometer, the atomizer 2 will be required to be heated through three temperature ranges which are identified as the dry, ash and atomizing temperature ranges. When the atomizer 2 is to be operated in the "dry" mode, which is the low temperature range of operation, $V_E$ will be close to the bottom of the sawtooth wave form of FIG. 5, and consequently, the S.C.R. 5 will conduct for a small period of time only. Since the base voltage of the signal of the ramp generator 6 is above zero as previously explained, very fine control of the atomizer heating is possible in the low temperature range. That is, $V_E$ can be conveniently moved into and out of the sharp lower zone of the ramp generator signal to achieve fine control of the S.C.R. conduction.

If $V_E$ moves towards the maximum permitted by the circuitry, circuit tolerances are such that it could move above the predetermined maximum $V_{p2}$, and in normal circumstances that would cause the S.C.R. 5 to move instantaneously from full drive conduction to no conduction, in which event control of the atomizer temperature would be lost. The distorted ramp generator wave form achieved by the attenuator 14 however, provides a safety margin above $V_{p2}$ which is represented by the pips 15. Thus, if $V_E$ rises above $V_{p2}$ there will be substantially full drive conduction of the S.C.R. 5, and the off-time of the S.C.R. 5 is determined by the width of the pips 15.

It will be appreciated from the foregoing that the invention provides a valuable and effective means of maintaining a relatively stable temperature in a carbon rod or other flameless atomizer. Thus, when applied to spectrophotometers and other chemical analysis apparatus, the invention improves the accuracy of the analysis.

In the circuit particularly described, the resistance $R_F$ has been described as a fixed resistance. It is to be appreciated however, that in some circumstances the heater circuit might be arranged so that the resistance $R_F$ is variable to suit changing conditions of use.

Finally, it is to be understood that various alterations, modifications and/or additions may be introduced into the constructions and arrangements of parts previously described without departing from the spirit or ambit of the invention as defined by the appended claims.

Having now described our invention, what we claim as new and desire to secure by Letters Patent is:

1. Chemical analysis apparatus including; an atomizer for receiving a sample to be analysed; a heater circuit which includes said atomizer and is connectable to an electrical power source so that said atomizer is heated by resistance heating, the total electrical resistance of said circuit being the sum of the atomizer resistance and a further resistance which is the electrical resistance of that part of said circuit other than said atomizer, and said further resistance is preselected relative to said atomizer resistance such that operational variations of said atomizer resistance do not substantially affect power dissipation in said atomizer during heating thereof; and a feed-back system connectable to said power source and being operative to maintain a substantially constant voltage across said heater circuit during heating of said atomizer.

2. Chemical analysis apparatus according to claim 1, wherein said resistance connected in series is formed at least in part by the inherent resistance of the electrical circuit through which said power source is connected to said atomizer to cause said heating thereof.

3. Chemical analysis apparatus according to claim 2, wherein said electrical resistance connected in series has a resistance value no less than half and no more than twice the resistance value of said atomizer.

4. Chemical analysis apparatus according to claim 3, wherein the two said resistance values are substantially equal.

5. Chemical analysis apparatus according to claim 1 wherein said feed-back system includes, a reference voltage source, a comparator operative to produce a pulsed signal which is characteristic of the difference between the reference voltage and the voltage applied to the atomizer, and control means responsive to said pulsed signal to modify said applied voltage as required.

6. Chemical analysis apparatus according to claim 5, wherein said applied voltage is an A.C. voltage, and said feed-back system includes triggering means which regulates said control means so that said response occurs at an appropriate time in each cycle of the A.C. supply resulting in the applied voltage.

7. Chemical analysis apparatus according to claim 6, wherein; said feed-back system further includes summing means which is operative to produce an error signal representative of the difference between said reference and applied voltages, said control means comprises a silicon controlled rectifier, said triggering means includes a ramp generator, and said comparator responds to both said error signal and a signal from said ramp generator to produce said pulsed signal.

8. Chemical analysis apparatus according to claim 7, wherein said ramp generator includes, a zero crossing detector operative to produce a signal each time the voltage of said power supply reaches zero, amplifying means responsive to said zero crossing detector signal to produce a ramped voltage signal which periodically shorts to a minimum value no less than zero, and an attenuator operative to distort each peak of said ramped voltage signal to create a narrow zone above that peak, which peak is representative of the expected maximum of said error signal, and each said zone is representative of the "off-time" of said silicon controlled rectifier when said error signal exceeds said expected maximum, whereby said silicon controlled rectifier is maintained at substantially full drive conduction if said expected maximum is exceeded.

9. Chemical analysis apparatus including; an atomizer for receiving a sample to be analyzed and being connectable to an electrical power source so as to be heated by resistance heating; an electrical resistance connected in series with said atomizer and having a resistance value which is within the range of 2.0–0.5 inclusive of the initial resistance value of said atomizer; said atomizer and said electrical resistance forming a heater circuit; and a voltage feed-back circuit connected across said atomizer and being operative to maintain a substantially constant voltage across said heater circuit during heating of said atomizer.

10. In a spectrophotometer, an atomizer and a heater circuit for said atomizer which is connectable to an electrical power source so as to cause heating of said atomizer by resistance heating, said circuit including components connected in series with said atomizer and which have a combined electrical resistance value no less than half and no greater than twice the resistance value of said atomizer, and a feed-back system comprising, a reference voltage source, means operative to produce an error signal when a difference occurs between the reference voltage and the voltage applied to said atomizer, and control means responsive to said error signal to modify said applied voltage as required.

11. A method of sample analysis including the steps of, connecting an atomizer in series with an electrical resistance having a resistance value no less than half and no more than twice the resistance value of said atomizer; said atomizer and said electrical resistance forming a heater circuit; connecting said heater circuit to an electrical power source to heat said atomizer by electrical resistance heating; maintaining a substantially constant voltage across said heater circuit; and introducing a sample to be analyzed to said heated atomizer.

* * * * *

UNITED STATES PATENT AND TRADEMARK OFFICE

CERTIFICATE OF CORRECTION

PATENT NO. : 4,134,685

DATED : January 16, 1979

INVENTOR(S) : E. G. Egan et al

It is certified that error appears in the above-identified patent and that said Letters Patent are hereby corrected as shown below:

Insert -- Foreign Application Priority Data   Oct. 18, 1976

7757/76 Australia -- on the title page of the printed patent.

Signed and Sealed this

Twenty-fifth Day of September 1979

[SEAL]

Attest:

LUTRELLE F. PARKER

Attesting Officer   Acting Commissioner of Patents and Trademarks